(12) United States Patent
Peukert

(10) Patent No.: US 9,456,859 B2
(45) Date of Patent: Oct. 4, 2016

(54) READJUSTABLE POLYAXIAL PEDICLE SCREW

(75) Inventor: Andrea Peukert, Tuttlingen (DE)

(73) Assignee: Aesculap AG (DE)

( * ) Notice: Subject to any disclaimer, the term of this patent is extended or adjusted under 35 U.S.C. 154(b) by 141 days.

(21) Appl. No.: 14/348,279

(22) PCT Filed: Aug. 2, 2012

(86) PCT No.: PCT/EP2012/065196
§ 371 (c)(1),
(2), (4) Date: Jul. 9, 2014

(87) PCT Pub. No.: WO2013/050187
PCT Pub. Date: Apr. 11, 2013

(65) Prior Publication Data
US 2014/0358182 A1    Dec. 4, 2014

(30) Foreign Application Priority Data
Oct. 5, 2011 (DE) .......... 10 2011 054 203

(51) Int. Cl.
*A61B 17/86* (2006.01)
*A61B 17/70* (2006.01)
*A61B 17/00* (2006.01)

(52) U.S. Cl.
CPC ....... *A61B 17/8605* (2013.01); *A61B 17/7002* (2013.01); *A61B 17/7032* (2013.01); *A61B 17/7037* (2013.01); *A61B 2017/0023* (2013.01)

(58) Field of Classification Search
CPC .......... A61B 17/7037; A61B 17/7032; A61B 17/7002; A61B 17/8605; A61B 2017/0023; A61B 2019/307
USPC ................. 606/246–291, 300–315
See application file for complete search history.

(56) References Cited

U.S. PATENT DOCUMENTS

| | | | | |
|---|---|---|---|---|
| 5,681,319 A | * | 10/1997 | Biedermann | A61B 17/7037 606/104 |
| 2005/0187548 A1 | * | 8/2005 | Butler | A61B 17/7032 606/278 |

(Continued)

FOREIGN PATENT DOCUMENTS

| | | |
|---|---|---|
| DE | 195 07 141 A1 | 9/1996 |
| DE | 69630957 | 10/2004 |

(Continued)

OTHER PUBLICATIONS

International Search Report issued in related Application No. PCT/EP2012/065196, mailed Oct. 19, 2012.

(Continued)

*Primary Examiner* — Pedro Philogene
(74) *Attorney, Agent, or Firm* — RatnerPrestia

(57) ABSTRACT

A polyaxial pedicle screw includes a threaded shaft portion for anchoring the pedicle screw in a vertebra, the pedicle screw having one axial end provided with a shaft head which is coupled to a mounting sleeve for a longitudinal beam in a rotatable and/or pivotable manner, including a fixing device for the selective positional fixation of the mounting sleeve with respect to the shaft portion. The fixing device includes a locking element as well as a counterforce part which is formed so as to be separate from the pedicle screw and counteracts the holding force of the locking element, preferably a grub screw or threaded nut, and is designed and/or retained in such a manner that the holding force of the locking element can be selectively released by means of the counterforce part, viz. is without any effect.

15 Claims, 4 Drawing Sheets

(56) References Cited

U.S. PATENT DOCUMENTS

Figure 2:
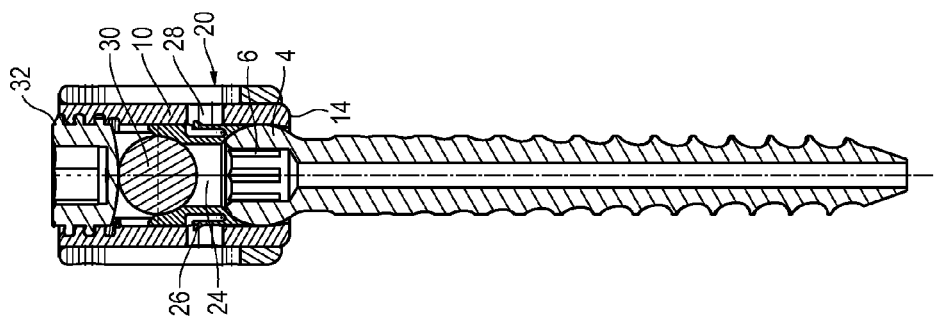

| | | | | |
|---|---|---|---|---|
| 2005/0267472 A1* | 12/2005 | Biedermann | ...... | A61B 17/7037 606/308 |
| 2008/0215100 A1* | 9/2008 | Matthis | ............ | A61B 17/7032 606/309 |
| 2009/0069852 A1 | 3/2009 | Farris | | |
| 2010/0114180 A1* | 5/2010 | Rock | ................. | A61B 17/7037 606/308 |
| 2011/0046683 A1* | 2/2011 | Biedermann | ...... | A61B 17/7035 606/305 |

FOREIGN PATENT DOCUMENTS

| | | |
|---|---|---|
| DE | 60018450 T2 | 2/2006 |
| EP | 2 301 458 A1 | 3/2011 |
| JP | 2007510468 | 4/2007 |
| JP | 2010537780 | 12/2010 |
| WO | 2005041821 | 5/2005 |

OTHER PUBLICATIONS

German Search Report issued in related German Application No. 10 2011 054 203.5, dated Jun. 14, 2012 (with English language description of category codes).

Japanese Office Action mailed May 31, 2016 for Japanese Application No. 2014-533808, including English translation, 9 pages.

* cited by examiner

READJUSTABLE POLYAXIAL PEDICLE SCREW

RELATED APPLICATIONS

This application is the U.S. National Phase of International Application No. PCT/EP2012/065196, filed Aug. 2, 2012, which claims the benefit of priority of German Application No. 10 2011 054 203.5, filed Oct. 5, 2011, the contents of both applications being incorporated by reference herein in their entirety and for all purposes.

FIELD

The present invention generally relates to a polyaxial pedicle screw and in particular to a readjustable polyaxial pedicle screw as well as to a corresponding vertebral stabilizing system.

BACKGROUND

Pedicle screws basically serve the dorsal stabilization of the vertebral column in case of fractures, tumors, inflammations, deformities and degenerative instabilities by means of a transpedicular screw connection system. In this arrangement, pedicle screws are placed in the pedicles of neighboring vertebrae, creating an angularly stable connection between the pedicle screws arranged axially one upon the other and an axially extending longitudinal beam or web. In such arrangement, the pedicle screws and the longitudinal beam form a vertebral stabilizing system.

To this end, a pedicle screw usually has an axial, shaft-like external thread portion adjoined by a so-called tulip at the side of the screw head. The structure of said tulip forms a U-shaped mounting sleeve which is slotted/tunneled in the longitudinal direction and comprises an internal thread, with the two opposite longitudinal slots each defining a slot gap with a predetermined gap width. The longitudinal beam is inserted in the longitudinal slots extending parallel to each other and is fixed by means of a grub screw or threaded nut which is screwed in the internal thread.

In principle, pedicle screws are grouped in two basic types, namely mono-axial and polyaxial pedicle screws. In the case of a mono-axial pedicle screw, the external thread portion and the tulip are formed in one piece with each other such that they are firmly connected to each other, for instance welded or soldered. A polyaxial pedicle screw, however, comprises an external thread portion which is manufactured as a separate shaft piece and has a mostly ball-shaped or (semi) spherical screw head which is encompassed by the sleeve-shaped tulip in a relatively pivotable manner and at the same time engaged by the latter in the transition area between head and shaft. In this way, the tulip can be swiveled and/or rotated relative to the shaft after having lowered the external thread portion in the pedicle channel of a vertebra, in order to obtain a desired position and alignment substantially regardless of the alignment relative to the shaft. Here, the undercut prevents the tulip from being pulled off the shaft head. Subsequently, the tulip is fixed in its position on the screw head by means of the grub screw with an interposed web (single-screw principle) or through an additional screw/screw nut (multi-screw principle).

The prior art discloses, for instance according to EP 2 301 458 A1, a polyaxial pedicle screw according to the single-screw principle consisting of a shaft piece comprising an external thread and a spherical head as well as a U-shaped mounting sleeve (tulip) provided with a longitudinal slot and intended for receiving a longitudinal beam/web. In the axial area toward the opening of the longitudinal slots, the mounting sleeve has an internal thread for screwing in a grub screw, and in the axial area toward the respective slot base it comprises a circumferential protrusion or shoulder with radially inward orientation. Further, a sort of piston or punch (also referred to as an inlay) is inserted in the mounting sleeve so as to be axially shiftable therein and prevented from falling out by means of a snap ring.

For assembling the polyaxial pedicle screw known from EP 2 301 458 A1, the mounting sleeve is first slipped over the shaft piece starting from the distal end thereof (the end which is opposite the shaft head) until the radially inward shoulder of the mounting sleeve abuts against the shaft head (at its underside). Subsequently, the punch will be pressed into the mounting sleeve (above the shaft head), so that the snap ring circumferentially arranged between the mounting sleeve and the punch snaps in place in corresponding circumferential grooves on the punch and on the mounting sleeve and retains the two parts axially next to each other. Thus, the shaft head is situated between the shoulder and the punch (i.e. underneath the punch).

As soon as the pedicle screw has been screwed in a vertebra and firmly anchored therein, a longitudinal beam is inserted in the U-shaped (double) slot of the mounting sleeve (above the punch), with the possibility that the mounting sleeve can rotate and swivel relative to the anchored shaft piece. This allows a surgeon to adapt the mounting sleeve in accordance with the alignment of the longitudinal beam. As soon as the suitable relative position of the mounting sleeve is adjusted, the grub screw is screwed into the mounting sleeve until it makes the longitudinal beam contact the punch and presses the latter farther in the axial direction of the mounting sleeve against the shaft head. In this way, the entire system made up of the pedicle screws and the longitudinal beam (vertebral stabilizing system) can be fixed in the adjusted position by tightening the single grub screw.

The document US 2011/0046683 A1 discloses e.g. a polyaxial pedicle screw according to the multi-screw principle. This pedicle screw, too, has a shaft-like external thread portion comprising an integral shaft head at a proximal end of the shaft. The shaft head is surrounded by a freely rotatable and pivotable mounting sleeve which is likewise provided with an internal thread and comprises two U-shaped opposing longitudinal slots for a longitudinal beam.

A piston/punch (inlay) is inserted in the mounting sleeve so as to be axially shiftable therein and is likewise provided with a U-shaped longitudinal slot having approximately the same slot width dimensions as the longitudinal slots in the mounting sleeve.

For the purpose of assembling the pedicle screw known from US 2011/0046683 A1, the mounting sleeve/tulip is slipped over the shaft in a known manner until it rests axially at the shaft head (at the underside) against a radially inward sleeve shoulder in pivotable and rotatable manner. As a next step, the punch (above the shaft head) is inserted in the mounting sleeve and its U-shaped slot is aligned in accordance with the U-shaped slots in the mounting sleeve. A first screw/screw sleeve will then be screwed in the mounting sleeve, directly acting on the punch (inlay) in order to press the latter against the shaft head, if necessary. This first screw/screw sleeve has an internal thread into which a second screw/grub screw is screwed which exerts a compressive force on a web/longitudinal beam transversely inserted in the longitudinal slot of the mounting sleeve and of the punch, to clamp the beam against the punch.

If the pedicle screw according to US 2011/0046683 A1 is to be inserted in a vertebra, the shaft is screwed in the vertebra and then the angular orientation of the mounting sleeve is aligned relative to the screwed-in shaft. In order to fix the position of the mounting sleeve, the first screw will then be tightened and presses the punch (inlay) directly against the shaft head and thereby braces the mounting sleeve with the shaft head. Finally, a longitudinal beam is placed in the longitudinal slot between the shaft head and the first screw in transverse orientation and is clamped against the punch by means of the second screw. Consequently, the advantage of this pedicle screw according to US 2011/0046683 A1 is that the processes of fixing the polyaxial support and the longitudinal beam are carried out independently of each other, but a comparably complicated screw design is required here.

Furthermore, all the mentioned pedicle screws have their fixing devices/locking elements (screws) realized in a substantially self-locking design, so as to avoid the risk of an unwanted detachment of the longitudinal beam from the pedicle screws after implantation. Further, the fixation forces between the pedicle screw and the longitudinal beam are large, as the entire system has to withstand high loads providing that the adjusted positional relation between the shaft, the sleeve and the longitudinal beam does not change. These requirements, however, cause problems during the implantation process.

If it has happened that a surgeon has tightened the locking element (for example the grub screw) with force, the resultant positional relation between the mounting sleeve and the shaft and/or between the mounting sleeve and the longitudinal beam cannot be altered any more or only with large effort. In other words, the surgeon would have to unloose the screw(s) (which has/have been tightened with high force) against the self-locking effect, without detaching the external thread portion already anchored in the vertebra or even breaking it out. Further, any subsequent process of unloosing the locking element (screw) might have a negative impact on its self-locking effect, so that the functionality of the pedicle screw as a whole is not ensured any more. This is why the known systems are not fault-tolerant or only to a limited extent.

SUMMARY

In view of the problems described above, it is an object of the invention to provide a polyaxial pedicle screw whose fixing device is prepared for releasing and again establishing a state of fixation. An objective of the invention is to put a surgeon in a position to continue to set the pedicle screw in the usual way, without the need of carrying out additional operation steps as with known screws. Further, it is an objective of the present invention to design the pedicle screw and in particular its fixing device in a fault-tolerant manner such that an already fixed polyaxial support can be nullified (unlocked) at a later point in time and then be fixed (locked) again.

The above-mentioned object is achieved by a polyaxial pedicle screw (preferably according to the single-screw principle) as well as by a vertebral stabilizing system comprising features described herein.

In principle, the gist of the invention is to furnish the fixing device of the pedicle screw (of known construction as described above) with an external/separate (additionally activatable) counterforce part which counteracts the holding force of a locking element of the fixing device, for instance of the grub screw or threaded nut, and which is designed and/or retained such that the holding force of the locking element can be selectively released (i.e. the function of the locking element can be suspended) by means of the counterforce part (by manually operating the counterforce part).

Thus, this basic principle of the invention is based on the thought to use the locking element of the fixing device in preferably known design for a customary positional fixation of the adjusted polyaxial support, while the counterforce part of the fixing device is in a quasi engaged state/position in which the locking element can fulfill its function. For releasing the state of fixation, however, not the locking element shall be (manually) released, but the counterforce part is moved or switched to a quasi uncoupled state/position in which the function of the locking element is neutralized/reduced. This allows to unmake the state of fixation merely by actuating the counterforce part and to establish it again without the need of actuating the locking element. As an alternative or in addition, there is also the possibility to unlock the locking element substantially without any effort, i.e. to move it to its unlocking position, without affecting the self-locking effect of the locking element (as already substantially free of any force). In this case, the counterforce element may then again be transferred to its coupled state in a forceless manner, whereupon the locking element will be actuated for fixing the polyaxial support.

More specifically, the locking element, for example a grub screw, is screwed as usual directly into the tulip and presses the punch axially against the shaft head preferably via the inserted longitudinal beam, to brace the tulip (and the longitudinal beam) preferably according to the single-screw principle with the screw head. The counterforce element has the effect that the preload force is applied to the screw head and/or transferred into the tulip. If the counterforce element is taken out of function, the punch and/or the locking element yield(s) in radial direction and the (axially acting) preload force is nullified abruptly.

The previously described basic principle maintains the functionality of the locking element in principle. Simultaneously, the risk of damaging or loosening the anchoring of the pedicle screw, according to the invention, in the vertebra is significantly reduced compared to the prior art.

Provision can be further made for the separate counterforce part to design it as a disposable part, which can be uncoupled accordingly only by destroying it; thereafter, it is replaced by a replacement part. Alternatively, the counterforce part may be provided with an opening mechanism by means of which the counterforce part can be altered in terms of its dimensions, in order to be able to be reversibly converted from a coupling shape (coupling dimension) into an uncoupling shape (uncoupling dimension). Alternatively or in addition, it is also possible to movably support the counterforce part in such a manner that it can be shifted from a functional position (a position in which a counterforce is produced) into a non-functional position (position with no counterforce).

Depending on the type of the polyaxial pedicle screw, the counterforce part may act (exclusively only) on the fixation mechanism of the fixing device for the positional fixation of the tulip (mounting sleeve) with respect to the shaft and/or on the fixation mechanism of the fixing device for the positional fixation of the tulip with respect to a longitudinal beam.

One aspect of the invention makes provision to design the counterforce part as a tensioning or clamping device, being able to selectively maintain the shape and/or function of the tulip (mounting sleeve) and/or of the punch of a polyaxial pedicle screw which is known per se according to the previous description.

It is preferred that the counterforce part is a (tensioning) ring which is guided preferably at the outside around the tulip (mounting sleeve) and/or the punch (in the area of the shaft heads) and is capable of exerting a radially inward (counter) force on the tulip and/or the punch.

It is further preferred that the ring is supported so as to be axially shiftable, so that it can be selectively moved to the functional position (in the axial area of the shaft head) or the non-functional position (displaced with respect to the axial area of the shaft head). As an alternative to this, the ring may be provided with an opening or width adjustment mechanism, to selectively move the ring to the functional or non-functional position by its inner design, so to speak. The simplest alternative may provide for manufacturing the ring from a destroyable material, which can be readily destroyed by hand, or to realize it with a manually activatable predetermined breaking point. This allows for the destruction of the ring without damaging the anchoring.

It is of advantage to provide the tulip (mounting sleeve) and/or the punch at least in the area of the counterforce part, preferably in the form of the tensioning and/or clamping device and more preferably of the tensioning ring, with resilient features. To this end, provision can be made to shape the tulip and/or the punch with longitudinal slots, creating lugs which can be elastically bent outside in the radial direction and are selectively kept together in the radial direction by the counterforce part according to one of the preceding embodiments. Alternatively, it is also possible to provide the material of the tulip and/or of the punch at least in zones with resilient properties. These lugs preferably have radial inward shoulders (claws) which can reach behind the shaft head and hence transmit a clamping axial force to the shaft head, in fact whenever the tensioning ring (in its functional position) prevents a radial spreading of the lugs.

In the case of the previously mentioned axial displacement of the tensioning ring, two axially spaced latching positions may be formed on the tulip and/or on the punch, to mark the functional and non-functional positions. Here, it is explicitly referred to the fact that the mentioned capability of the tensioning ring to shift in the axial direction may also be replaced by a rotatability to define the functional and non-functional positions.

In the end, it is basically also possible to realize the counterforce part as an insertable and selectively actuatable threaded sleeve which is latched in place in the tulip and/or the punch. In this case, the threaded sleeve transfers the (axial) force from the locking element (grub screw) to the mounting sleeve or punch. For releasing the locking element, the mutual latching between the mounting sleeve and the threaded sleeve inserted therein is disengaged by hand and hence the locking element is changed to a forceless state.

BRIEF DESCRIPTION OF THE DRAWING FIGURES

Figure 1B:
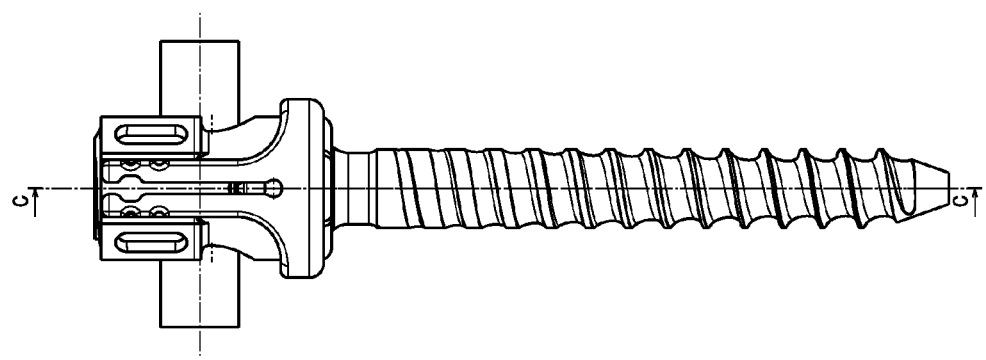
Figure 1A:
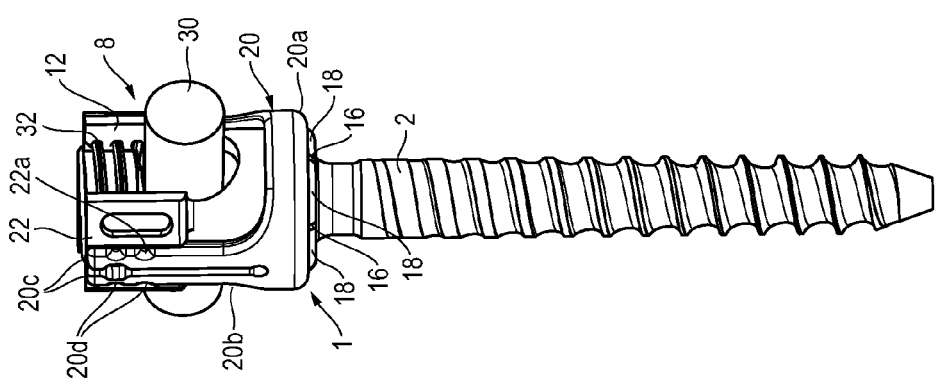
Figure 4:
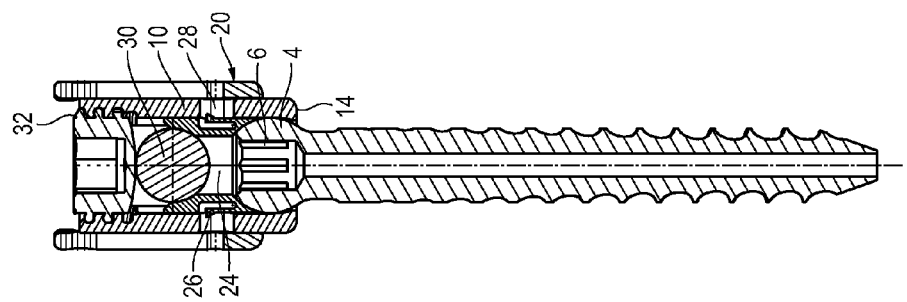
Figure 3B:
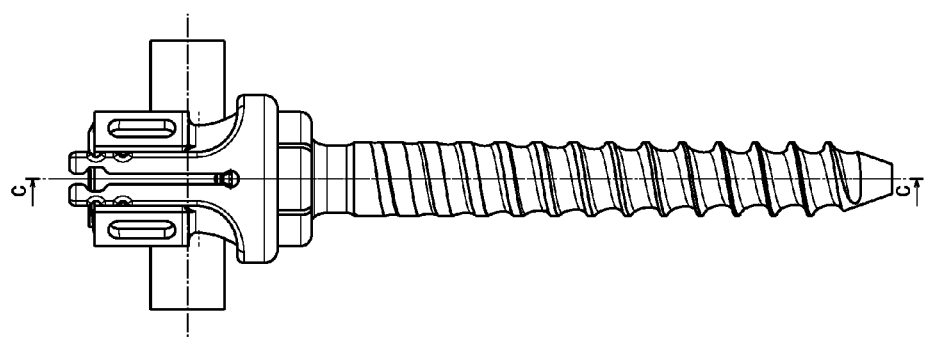
Figure 3A:
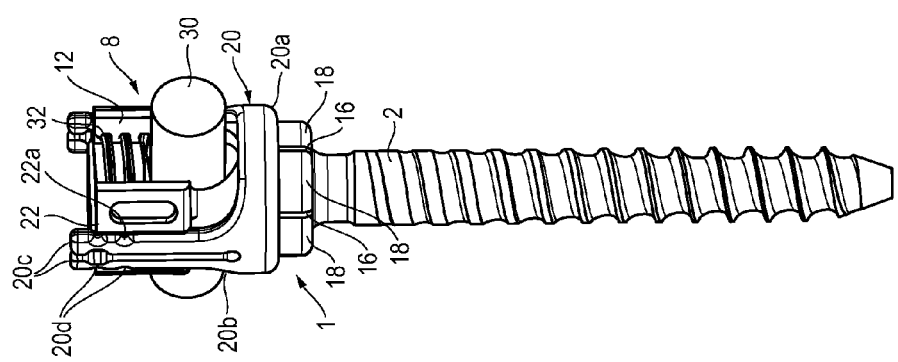
Figure 5:
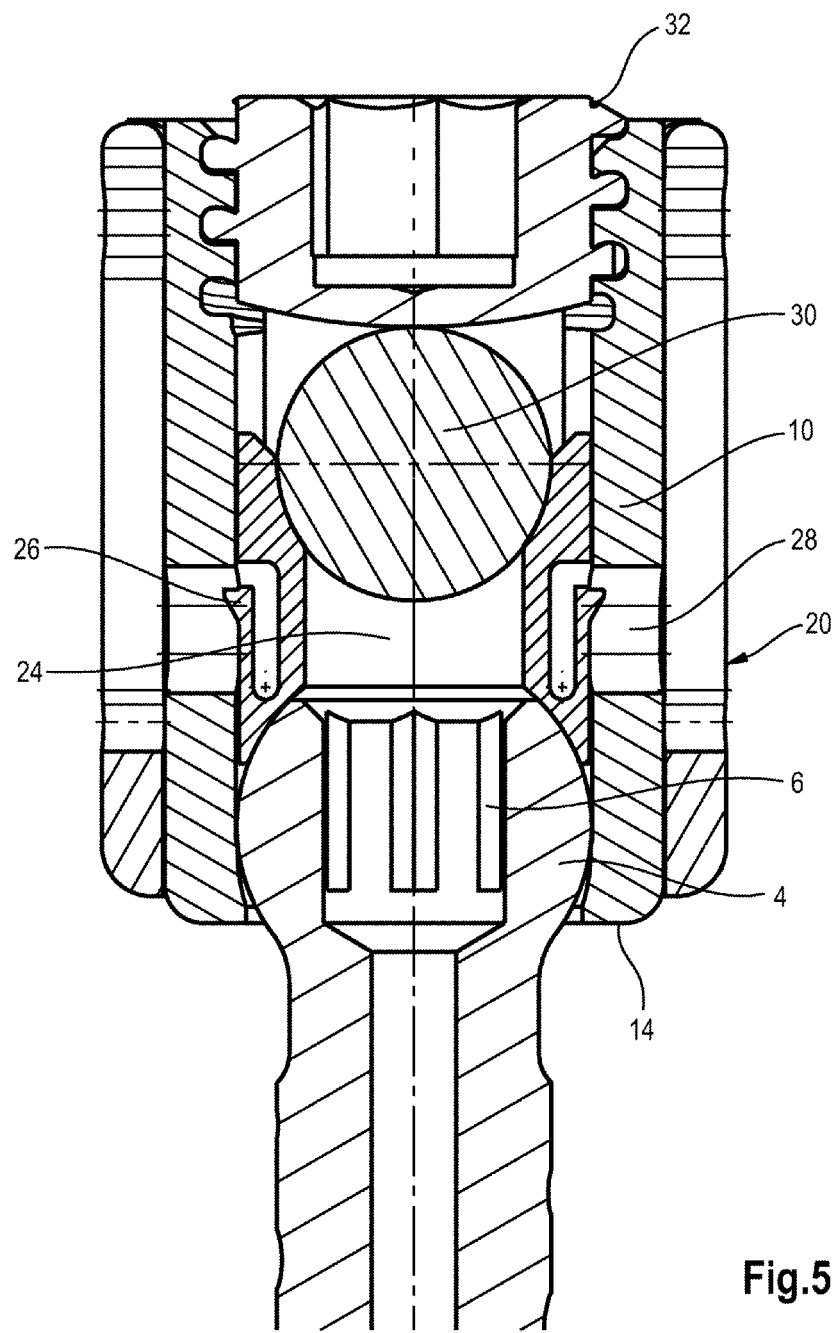
Figure 6:
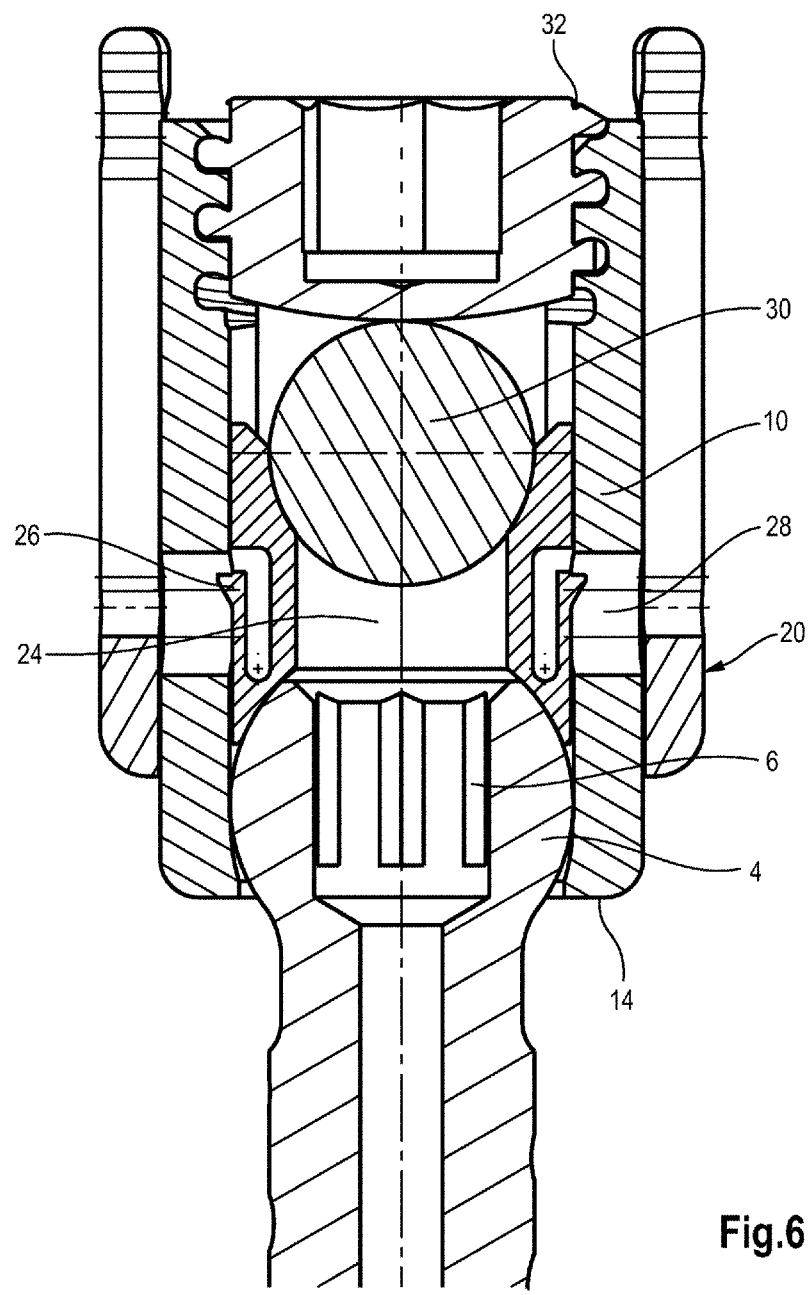

The invention will be explained in more detail below on the basis of a preferred exemplary embodiment with reference to the accompanying Figures in which:

FIG. 1a-1b each show a perspective view of a vertebral stabilizing system according to a preferred exemplary embodiment of the invention consisting of a polyaxial pedicle screw and a schematically illustrated longitudinal beam in a functional position, FIG. 2 shows a longitudinal section of the vertebral stabilizing system according to FIG. 1, FIG. 3a-3b each show a perspective view of the vertebral stabilizing system according to the preferred exemplary embodiment of the invention in a non-functional position, FIG. 4 shows a longitudinal section of the vertebral stabilizing system according to FIG. 3, FIG. 5 shows the mounting sleeve in a locked state in an enlarged presentation, and FIG. 6 shows the mounting sleeve in an unlocked state in an enlarged presentation.

DETAILED DESCRIPTION

The vertebral stabilizing system according to the preferred exemplary embodiment of the invention and shown in FIG. 1a-1b comprises a polyaxial pedicle screw 1 consisting of an externally threaded shaft or anchor 2 which has a proximal end on which a preferably spherical or at least semi-spherical shaft head 4 is formed or integrally formed. Provided in the shaft head 4 is a tool engagement feature 6, for instance for an Allen wrench, a Philips screwdriver etc., in order to be able to screw the shaft 2 into the pedicle channel of a vertebra (not illustrated).

As can be seen in FIG. 2, the shaft head 4 forms at its transition area to the threaded shaft/shaft portion 2 an undercut acting in the axial direction. In the present case, said undercut is produced by the fact that the shaft head diameter is selected so as to be larger than the shaft diameter. Alternatively, it would also be conceivable to form the shaft head 4 with respect to the remaining threaded shaft portion 2 by means of a lathed groove (not shown) at the proximal end portion of the shaft 2.

According to FIGS. 1a-1b and 2, the shaft head 4 is enclosed by a mounting sleeve 8 which (for a start) is rotatable and retained by the shaft head 4 in pivotable manner.

Specifically, the mounting sleeve 8 comprises a cylindrical sleeve body 10 which is open at both sides and whose sleeve wall is provided with a U-shaped slot starting from the proximal end face, resulting in a continuous transverse channel (slot) 12 extending substantially perpendicular to the sleeve axis. In the axial area toward the open side of the U-shaped slot 12, the mounting sleeve 8 is provided with an internal thread which extends according to the FIG. 2 approximately as far as to an axial center portion of the sleeve 8. In the opposite axial area (in other words, at the axially distal end) of the sleeve 8, i.e. axially behind the slot base of the U-shaped slot 12, the mounting sleeve 8 is provided with a circumferential inner radial protrusion/shoulder 14, constricting the inner diameter of the sleeve at the end face and thus forming an undercut. Here, the diameter of the inner radial protrusion 14 is sized such that it is slightly larger than the diameter of the threaded shaft portion 2, but smaller than that of the shaft head 4. Further, the inner diameter of the sleeve 8 is slightly larger than the diameter of the shaft head 4.

According to the invention, the mounting sleeve 8 is provided—at least in the axial area of its inner radial protrusion 14—with resilient or flexible features acting at least in the radial direction. In particular, the mentioned distal end zone of the mounting sleeve 8 comprises a number of longitudinal slots 16 spaced in the circumferential direction, resulting in a number of lug- or tongue-shaped sleeve portions 18 which extend parallel to each other in the axial direction and can be bent outward in an elastic/flexible manner. Here, it is referred to the fact that the mentioned flexible features may also be achieved in a somewhat different manner by design, for example by attaching a resilient collar (not shown) axially to the mounting sleeve 8 or by forming an open grid or spiral structure (likewise not shown) in the sleeve wall, etc.

Around the mounting sleeve 8, there is arranged a counterforce part 20 in the shape of a collar-like locating ring which is guided so as to be axially shiftable on the mounting sleeve 8 and encompasses the distal end portion, which can be radially spread in flexible/elastic fashion, of the mounting sleeve 8 in a first position (functional position) so as to have contact to it.

Specifically, the locating ring 20 consists of a ring portion 20a which is closed in the circumferential direction, with two diametrically opposing axial webs 20b preferably being molded in one piece on its end face so as point toward the internal thread portion of the mounting sleeve 8. Each of the axial webs 20b forms two axial, parallel spring tongues 20c which in the present exemplary embodiment comprise two axially spaced undercuts or notches 20d. In use, these notches 20d define a functional position (according to FIGS. 1a-1b and 2) and non-functional position (according to FIGS. 3a-3b and 4) of the locating ring 20. On the other hand, two diametrically opposite axial grooves 22 are formed on the outer face of the mounting sleeve 8 which serve for guiding the two axial webs 20b and comprise at least one latching protrusion (nub) 22a which is able to functionally engage the notches 20d of the axial webs 20b.

As an alternative to the previously described locating ring design shown in FIGS. 1a-1b and 2, it is also possible to realize the locating ring 20 with a predetermined breaking point (not illustrated) at which the locating ring 20, which in this case would basically be in the functional position shown in FIG. 1a-1b (i.e. is immovable), can be broken apart by means of a tool, for instance. It is also conceivable to combine the axial movability of the locating ring 20 with a rotation. In this case, a kind of bayonet lock (not shown) could be provided instead of the axial latching means illustrated in FIG. 1a-1b, which is disengaged by rotating the locating ring 20; thereupon, an axial displacement of the ring 20 along the mounting sleeve 8 is possible.

As illustrated in FIG. 2, a punch or stud 24 is inserted in the mounting sleeve 8 so as to be arranged in the axial area of the flexible lugs/tongues 18 in the sleeve 8. Here, the punch 24 has its perimeter side provided with at least one resilient detent 26 (according to FIG. 2, two detents are diametrically arranged) which protrudes in the radial direction and snaps in place in the installation position of the punch 24 in a radially aligned recess 28 on the inner side of the mounting sleeve 8. In this way, the at least one detent 26 forms a safety means hindering the punch 24 from falling out. At the same time, the radial recess 28 is sized such that the punch 24 is able to move by a predetermined distance axially within the mounting sleeve 8.

On the end face oriented toward the inward protrusion 14 of the mounting sleeve 8, the punch 24 is flat or spherical such that it is able to have a substantially planar/areal contact with the shaft head 4. On the other end face, the punch 24 is formed like a channel in such a manner that the circumferential surface of a round bar longitudinal beam or web 30 may have an areal contact with the punch 24. Finally, FIGS. 1a-1b and 2 show a locking element in the shape of a grub screw (or set screw) 32 which is threaded in the mounting sleeve 8 in the internal thread thereof and is able to act on the longitudinal beam 30 already placed in the U-shaped slot, in order to press it against the end face of the punch 24.

The mode of operation of the pedicle screw according to the invention and of the vertebral body stabilizing system according to FIG. 1a-1b to 6 will be described below.

The pedicle screw 1a-1b according to the invention is supplied with the locating ring 20 in the functional position according to FIGS. 1a-1b and 2 and is inserted in said state. In this functional position, the locating ring 20 encompasses the spring lugs 18 of the mounting sleeve 8 so that they cannot be bent or expanded radially or only to a negligible extent. This means that inner diameter of the mounting sleeve 8 and hence of the inner radial protrusion 14 is fixed. In this state, the mounting sleeve 8 encompasses the shaft head 4 in a rotatable as well as pivotable manner; at the same time, the inner radial protrusion 14 engages behind/below the shaft head 4 in the transition area to the threaded shaft portion 2. This allows for the transmission of a tensile force from the mounting sleeve 8 to the shaft head 4.

In case the pedicle screw 1 according to the invention is to be implanted, a surgeon screws it in the pedicle channel of a vertebra as he would do that with conventional pedicle screws according to the construction as described at the outset. This means that he uses a screwing tool (not shown) and inserts it in the tool engagement feature 6 on the shaft head 4 to apply a screwing force directly to the shaft 2. In this assembly stage, the punch 24—which is provided with an axial through-hole for the passage of the tool—may already be inserted in the mounting sleeve 8, so that the tool can engage the tool engagement feature 6 of the shaft head 4 straight through the punch 24. In this stage, however, the grub screw 32 is not screwed in yet.

As soon as the threaded shaft 2 is firmly screwed (anchored) in the vertebra, the punch (inlay) 24 is snapped in place in the mounting sleeve 8 and the grub screw 32 is screwed in by a short thread depth (preferably by means of a tool) such that there is a lateral through-hole between the punch 24 and the grub screw 32 in the mounting sleeve 8 whose opening length depends accordingly on the position or thread depth of the grub screw 32.

For the purpose of coupling several pedicle screws of the invention to one another, which are screwed in at different, axially spaced vertebrae, the longitudinal beam 30 is inserted in the lateral through-hole (i.e. the U-shaped slot 12) of the mounting sleeve 8 (between the punch 24 and the screw 32), and at the same time the mounting sleeve 8 is aligned relative to the shaft 2 (by rotating and swiveling). As an alternative to the previously described procedure, it is also possible and may be of advantage if the longitudinal beam 30 is first inserted in the lateral through-hole of the mounting sleeve 8 and then the grub screw 32 is set (preferably by means of a tool). This assembly variant has the advantage that the through-hole for inserting the longitudinal beam 30 is not unduly constricted by the grub screw 32 set in advance.

If the longitudinal beam 30 has been inserted according to one of the above variants and the grub screw 32 has been set, the (grub) screw 32 is tightened with the (screwing) tool. In doing so, said screw exerts a compressive force on the longitudinal beam 30, which will be transferred via the punch 24 further on to the shaft head 4 acting as an abutment. This means that the grub screw 32, while clamping the longitudinal beam 30, presses the punch 24 against the shaft head 4, whereby the latter is braced between the inner radial protrusion 14 of the mounting sleeve 8 and the punch 24. As the sleeve 8 cannot spread due to the presence of the stiffening locating ring 20 in the axial area of the radial protrusion (see in particular FIG. 5), a considerable preload force on the shaft head 4 can be realized which is sufficiently high to fix the location/position of the mounting sleeve 8 relative to the shaft 2 as well as the position of the longitudinal beam 30 even under load. The grub screw 32 is designed such that it will not come loose when subjected to an expectable load—i.e. it acts in self-locking manner. Further, the frictional connection between the mounting sleeve 8 and the shaft head 4 is such that said frictional connection will not become disengaged or hardly become disengaged even if the grub screw 32 is unscrewed.

With this, the implantation of the pedicle screw 1 according to the invention and of the vertebral stabilizing system is finished.

It may happen, however, that the seat of the pedicle screw 1 has to be corrected again at a later point in time. To this end, the locating ring 20 is switched from its functional position shown in FIGS. 1a-1b and 2 (radially around the radial protrusion) to its non-functional position shown in FIGS. 3a-3b and 4 (axially offset with respect to the radial protrusion). This state is shown in particular in FIG. 6 on an enlarged scale.

In other words, the locating ring 20 is moved—manually or with the aid of a lever tool which is not shown in more detail—along the external grooves 22 on the mounting sleeve 8 presently toward the grub screw 32 until the non-functional position is reached which is marked by the notches 20d in the longitudinal webs 20b. In this non-functional position according to FIGS. 3a-3b and 4, the locating ring 20 does not surround said axial portion of the mounting sleeve 8 (or only to a partial extent) in which the longitudinal lugs 18 are formed, so that the latter are able to radially bend outward in flexible manner, preferably in elastic fashion. This allows for the expansion of the inner diameter of the mounting sleeve 8 and in particular the inner diameter of the inner radial protrusion 14 at the distal free end of the lug 18 in this area, whereby the inner radial protrusion 14 of the mounting sleeve 8 could slip over the shaft head 4. This means that the locating ring 20, having compressed/retained the lugs 18 in the radial direction as a counterforce part for the locking element (grub screw) 32, has lost this function now, so that the clamping force of the grub screw (locking element) 32 is released. Hence, the polyaxial support of the screw 1 is not locked any longer.

At this moment, virtually no clamping force acts on the grub screw 32, so that it can be unscrewed almost without any effort. If the pedicle screw 1 and hence the polyaxial support is to be locked again, it is only needed to shift the locating ring 20 from its disengagement position substantially without any force to the functional position according to the above definition, whereupon the grub screw 32 can be tightened again. At this point, it is explicitly referred to the fact that it is not mandatory to actuate the screw 32. Rather, it may be sufficient to only switch the locating ring 20 into its disengagement position in which the tulip can move relative to the shaft, in order to then switch the locating ring 20 again to its engagement position (without actuating the screw) to fix the new relative position.

Finally and in brief, the present invention relates to a polyaxial pedicle screw 1 comprising the threaded shaft portion 2 for anchoring the pedicle screw 1 in a vertebra, said pedicle screw having one axial end provided with the shaft head 4 which is coupled to the mounting sleeve 8 for a longitudinal beam 30 in a rotatable and/or pivotable manner, comprising a fixing device (consisting of the locking element 32 and the counterforce part 20) for the selective positional fixation of the mounting sleeve 8 with respect to the shaft portion 2. According to the invention, the fixing device comprises a locking element, preferably a (grub) screw 32, as well as a counterforce part, preferably a (movable and/or rotatable) locating ring 20 which counteracts the holding force of the locking element, preferably the grub screw 32 or a threaded nut, and is designed and/or retained such that the holding force of the locking element 32 can be selectively released by means of the counterforce part 20, viz. is (almost) without any effect.

The invention claimed is:

1. A polyaxial pedicle screw comprising a threaded shaft portion for anchoring the pedicle screw in a vertebra, said pedicle screw having one axial end provided with a shaft head which is coupled to a mounting sleeve for a longitudinal beam in a rotatable and/or pivotable manner, comprising a fixing device for the selective positional fixation of the mounting sleeve with respect to the shaft portion, the fixing device comprising a locking element for exerting a holding force on the mounting sleeve as well as a separate counterforce part counteracting the holding force of the locking element and being designed and/or retained in such a manner that the holding force of the locking element can be selectively released by means of the counterforce part, wherein the counterforce part is designed as a manually destroyable disposable part and/or is provided with an opening mechanism by means of which the counterforce part can be altered in terms of its dimensions and/or is movably supported such that it can be moved from a functional position to a non-functional position.

2. The polyaxial pedicle screw according to claim 1, wherein the locking element is provided for a positional fixation of the adjusted polyaxial support if the counterforce part is in a force-receiving state or in a functional position, whereas the counterforce part is provided for neutralizing or reducing the function of the locking element if the latter is already in a state of fixation.

3. The polyaxial pedicle screw according to claim 1, wherein the counterforce part acts on the fixation mechanism of the fixing device for the positional fixation of the mounting sleeve with respect to the shaft portion and/or on the fixation mechanism of the fixing device for the positional fixation of the mounting sleeve with respect to a longitudinal beam.

4. The polyaxial pedicle screw according to claim 1, wherein the counterforce part is designed as a tensioning or clamping device which is selectively able to maintain the shape and/or the function of the mounting sleeve and/or of a punch which is supported in the mounting sleeve for transmitting a force from the locking element to the shaft head.

5. The polyaxial pedicle screw according to claim 1, wherein the counterforce part is a tensioning ring which is guided outside the mounting sleeve and/or a punch supported in the mounting sleeve so as to be axially movable therein and intended for transmitting a force between the locking element and the shaft head and is provided for applying a radially inward counterforce on the mounting sleeve and/or the punch depending on the adjusted shape and/or position.

6. The polyaxial pedicle screw according to claim 1, wherein the counterforce part is a threaded sleeve for receiving the locking element, which is selectively detachably latched in place in the mounting sleeve by a bayonet or clip lock, in order to transmit the preload force of the locking element arranged in the threaded sleeve to the mounting sleeve or to selectively release it.

7. The polyaxial pedicle screw according to claim 5, wherein the ring is supported so as to be axially shiftable on the outer face of the mounting sleeve, so that it can be selectively moved to the functional or non-functional position.

8. The polyaxial pedicle screw according to claim 5, wherein the ring is provided with an opening or width adjustment mechanism to selectively move the ring internally to the functional or non-functional position without axially shifting it.

9. The polyaxial pedicle screw according to claim 5, wherein the ring is made of a material which can be manually destroyed with a predetermined expenditure of force below the maximum load of the shaft portion or is provided with a manually activatable predetermined breaking point.

10. The polyaxial pedicle screw according to claim 5, wherein the mounting sleeve and/or the punch, at least in the area of the counterforce part, is in the form of the tensioning and/or clamping device in the form of the tensioning ring, and is/are provided with resilient features which act at least in the radial direction.

11. The polyaxial pedicle screw according to claim 10, wherein the mounting sleeve and/or the punch is/are realized with longitudinal slots, producing lugs which can be elastically bent radially towards outside and are selectively kept together in the radial direction by the counterforce part, or in that the material of the mounting sleeve and/or of the punch is radially resiliently expandable at least in sections.

12. The polyaxial pedicle screw according to claim 5, wherein two axially spaced latching positions are realized on the mounting sleeve and/or on the punch in order to mark the functional or non-functional position in case the tensioning ring is axially shiftable.

13. The polyaxial pedicle screw according to claim 1, wherein the counterforce part can be moved manually to a first, active position in which the locking element is able to develop its effect and to a second, inactive position, in which the locking element is not able to develop any effect.

14. The polyaxial pedicle screw according to claim 1, wherein the counterforce part receives radial forces in its first, active position so as to counteract a radial deformation of the mounting sleeve, and in its second, inactive position it permits a radial deformation of the mounting sleeve at a defined axial portion.

15. A vertebral body stabilizing system consisting of at least one longitudinal beam for the longitudinal interconnection of two vertebral bodies, and a number of polyaxial pedicle screws according to claim 1.

\* \* \* \* \*